(12) United States Patent
Kwon et al.

(10) Patent No.: US 12,048,774 B2
(45) Date of Patent: Jul. 30, 2024

(54) METHOD FOR DECOMPOSING PERACETIC ACID AND METHOD FOR CULTURING MICROORGANISMS USING SAME

(71) Applicant: N-CELL CO., LTD., Chungcheongbukdo (KR)

(72) Inventors: Jong-Hee Kwon, Jinju-si (KR); Chang-Ho Cho, Jinju-si (KR)

(73) Assignee: N-CELL CO., LTD., Chungcheongbuk-Do (KR)

( * ) Notice: Subject to any disclaimer, the term of this patent is extended or adjusted under 35 U.S.C. 154(b) by 251 days.

(21) Appl. No.: 17/419,931

(22) PCT Filed: Dec. 24, 2019

(86) PCT No.: PCT/KR2019/018348
§ 371 (c)(1),
(2) Date: Jun. 30, 2021

(87) PCT Pub. No.: WO2020/141779
PCT Pub. Date: Jul. 9, 2020

(65) Prior Publication Data
US 2022/0080066 A1    Mar. 17, 2022

(30) Foreign Application Priority Data

Dec. 31, 2018  (KR) .................. 10-2018-0174021
Dec. 20, 2019  (KR) .................. 10-2019-0172429

(51) Int. Cl.
*A61L 2/18* (2006.01)
*C07C 51/377* (2006.01)
*C12N 1/00* (2006.01)

(52) U.S. Cl.
CPC .............. *A61L 2/18* (2013.01); *C07C 51/377* (2013.01); *C12N 1/00* (2013.01); *A61L 2202/13* (2013.01)

(58) Field of Classification Search
CPC ..... A61L 2/18; A61L 2202/13; C07C 51/377; C07C 51/00; C12N 1/00; C12N 1/20; C12N 1/10; C12N 1/12; C12N 1/14; C12N 1/16; C12R 2001/89; C12M 1/12; C12M 37/00; C12M 99/00
See application file for complete search history.

(56) References Cited

U.S. PATENT DOCUMENTS

2003/0211169 A1   11/2003   Tabasso

FOREIGN PATENT DOCUMENTS

| KR | 10-2013-0087773 A |   | 8/2013 |
| KR | 10-2015-0097295 A |   | 8/2015 |
| TW |     201417846 A | * | 5/2014 |
| WO |     2018/032013 A1 |   | 2/2018 |

OTHER PUBLICATIONS

Wei, C et al. Assessment of the Fe3+-EDTA complex in UV-Fenton-like processes: the degradation of methylene blue. Applied Mechanics and Materials. 2014. 675-677: 395-400. (Year: 2014).*
Morelli, R et al. Fenton-dependent damage to carbohydrates: Free radical scavenging activity of some simple sugars. J. Agric. Food Chem. 2003. 51: 7418-7425. (Year: 2003).*
TW 201417846 A. English Machine Translation. Published May 16, 2014. (Year: 2014).*
Advanced Biomass R&D Center "Development of Microalgae Mass Production in Organic Wastewater and Integration System For Microalgae Cultivation/Harvest/Lipid Extraction with Low Energy Consumption" Government Project Stage 2 Report. Apr. 2, 2016. pp. 1-346 (For English Summary, see p. 10).
Sung M. G. et al. "A simple method for decomposition of peracetic acid in a microalgal cultivation system" Bioprocess and Biosystems Engineering 2015, vol. 38, pp. 517-522.
Sung M. G. et al. "Decomposition of peracetic acid after sterilization of a microalgal cultivation system" The Korean Society for Biotechnology and Bioengineering. Apr. 2014, p. 391.
Cho, Chang-Ho et al., "Growth medium sterilization using decomposition of peracetic acid for more cost-efficient production of omega-3 fatty acids by Aurantiochytrium", Bioprocess and Biosystems Engineering, vol. 41 (Mar. 2018), pp. 803-809.
Yuan, Z. et al. "Kinetics of peracetic acid decomposition: Part I: Spontaneous decomposition at typical pulp bleaching conditions", The Canadian Journal of Chemical Engineering, vol. 75 (Feb. 1997), pp. 37-41.

* cited by examiner

*Primary Examiner* — David W Berke-Schlessel
*Assistant Examiner* — Susan E. Fernandez
(74) *Attorney, Agent, or Firm* — Bridgeway IP Law Group, PLLC; Sang Ho Lee; Hyun Woo Shin

(57) ABSTRACT

The present invention relates to a method for decomposing peracetic acid and a method for culturing microorganisms using the decomposition method. The cultivation of microorganisms using the method of the present invention allows an effective removal of the peracetic acid used in a culture medium for sterilization.

14 Claims, 1 Drawing Sheet

METHOD FOR DECOMPOSING PERACETIC ACID AND METHOD FOR CULTURING MICROORGANISMS USING SAME

TECHNICAL FIELD

The present invention relates to a method for decomposing peracetic acid that includes mixing peracetic acid with water; and adding an iron ion, an alkali metal hydroxide, ethylenediaminetetraacetic acid (EDTA), and a sugar to cause a reaction and decompose the peracetic acid reactant into acetic acid, water and oxygen, and a method for culturing microorganisms using the decomposition method for peracetic acid.

BACKGROUND ART

In mass production of useful metabolites using various microorganisms in the bio industry, sterilization of culture media and reactors is of a great importance. Autoclaves are a conventional machine mainly used for this purpose to sterilize microbial culture media and reactors.

The sterilization of culture media and reactors in an autoclave is, however, problematic in that the sugar component of the culture medium reacts with one of the other components of the medium, proteins (peptone or yeast extract) at high temperature to cause the generation of toxic substances such as hydroxymethyl furfural (HMF) capable of hindering the growth of microorganisms and that the reactors are required to be made of materials resistant to heat and pressure like metals or glass.

A method of filtration is used to overcome the above problems and limitations. But, the filtration method causes an inconvenience of requiring a separate sterilization of the incubator and a risk of clogging and re-contamination during the filtration process and involves a limited size of the filter and a high cost, thus resulting in poor commercial availability.

In order to solve this problem, a sterilization method using peracetic acid (PAA) has been devised as described in Korean Laid-Open Patent Publication No. 10-2015-0097295, which discloses a method of sterilizing a photobioreactor using peracetic acid in the pure culture of microalgae that requires light. However, the prior document does not mention an increase in the decomposition efficiency of peracetic acid caused by EDTA and sugar (e.g., glucose, sucrose, and waste sugar) or a sterilization method for the medium containing a sugar and a nitrogen source (peptone, yeast extract, whey, etc.).

In the method for sterilizing a photobioreactor and a culture medium using peracetic acid, where the medium contains a sugar and a nitrogen source, high-concentration (5 mM or above) peracetic acid is needed for a complete sterilization. Particularly, the sterilization of a medium containing a nitrogen source causes generation of nitrogen oxide ($NO^{3-}$) by the peracetic acid, and the nitrogen oxide binds to iron ions to inhibit the catalytic reaction for decomposition of the peracetic acid. In this case, it takes more than one month to completely decompose the peracetic acid reactant only by natural decomposition or the catalytic reaction driven by iron and HEPES.

DETAILED DESCRIPTION OF THE INVENTION

Technical Task

It is an object of the present invention to provide a method for decomposing peracetic acid that includes the steps of: mixing peracetic acid with water; and adding an iron ion, an alkali metal hydroxide, ethylenediaminetetraacetic acid (EDTA), and a sugar to cause a reaction and decompose the peracetic acid into acetic acid, water and oxygen.

It is another object of the present invention to provide a method for sterilizing a medium that includes the steps of: adding peracetic acid to a medium containing a sugar and a nitrogen source to cause a reaction for sterilization; and adding an iron ion, an alkali metal hydroxide, and ethylenediaminetetraacetic acid (EDTA) as accelerators for decomposition of peracetic acid to the sterilized medium and causing a reaction between the peracetic acid and the accelerator for decomposition of peracetic acid in the medium to decompose the peracetic acid into acetic acid, water and oxygen.

It is further another object of the present invention to provide a method for culturing microorganisms that includes the steps of: adding a medium sterilized by the method of claim 6 to a bioreactor; and inoculating microorganisms into the added medium and conducting a pure cultivation.

Means of Solving the Task

In order to achieve the objects of the present invention, there is provided a method for decomposing peracetic acid that includes the steps of: mixing peracetic acid with water; and adding an iron ion, an alkali metal hydroxide, ethylenediaminetetraacetic acid (EDTA), and a sugar to cause a reaction and decompose the peracetic acid into acetic acid, water and oxygen.

The present invention also provides a method for sterilizing a medium that includes the steps of: adding peracetic acid to a medium containing a sugar and a nitrogen source to cause a reaction for sterilization; and adding an iron ion, an alkali metal hydroxide, and ethylenediaminetetraacetic acid (EDTA) as accelerators for decomposition of peracetic acid to the sterilized medium and causing a reaction between the peracetic acid and the accelerator for decomposition of peracetic acid in the medium to decompose the peracetic acid into acetic acid, water and oxygen.

Besides, the present invention provides a method for culturing microorganisms that includes the steps of: adding a medium sterilized by the method of claim 6 to a bioreactor; and inoculating microorganisms into the added medium and conducting a pure cultivation.

Effects of the Invention

The present invention is directed to a decomposition method for peracetic acid and a method for culturing microorganisms using the decomposition method. The cultivation of microorganisms using the method of the present invention allows a complete sterilization of a bioreactor and a culture medium without heat and effectively removes the peracetic acid remaining in the medium used as a chemical sterilizer by decomposition rather than using sterilized washing water.

BEST MODE FOR THE IMPLEMENTATION OF THE INVENTION

Figure 1:
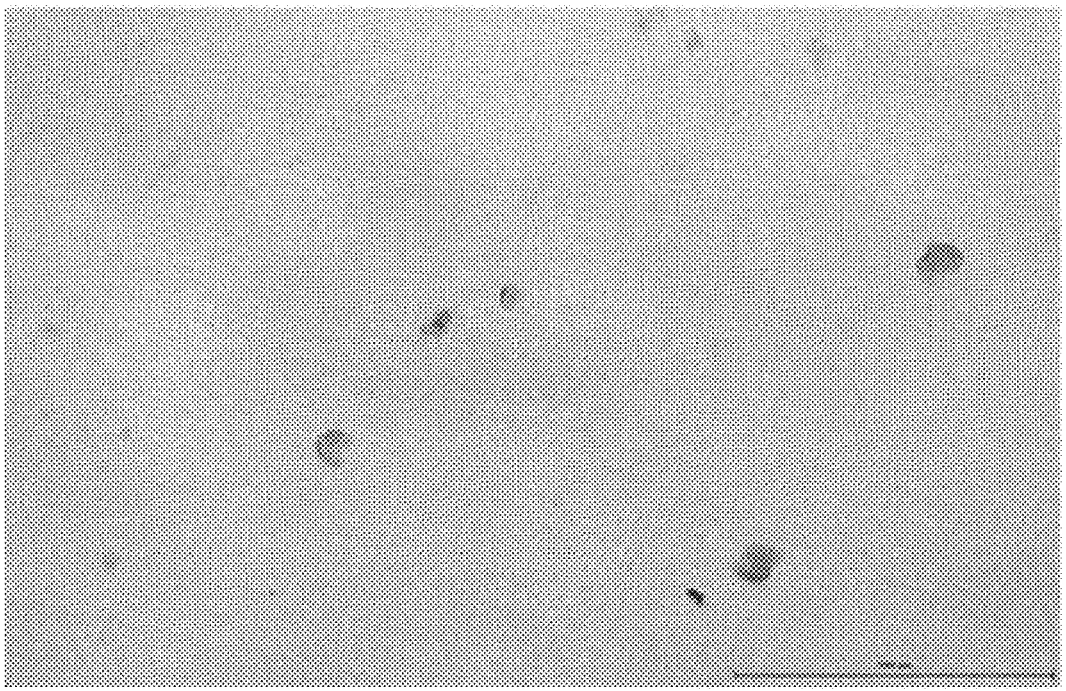
FIG. 1 is a microscopic image showing the agglomeration of iron ions during decomposition of peracetic acid without EDTA.

Hereinafter, the present invention will be described with reference to embodiments.

The embodiments are given for exemplary illustration of the present invention and construed not to limit the contents of the present invention.

Example 1: Confirmation of Decomposition of Peracetic Acid

Peracetic acid (Dong Myung ONC Corp., 160126) was added to 1 L of an *Aurantiochytrium* medium to have a concentration of 10.52 mM, and a reaction was caused for sterilization for 2 hours. To the medium sterilized with the peracetic acid were added 96 uM of $FeCl_3$ (Sigma, 7705-08-0), 5.5 mM of NaOH (Sigma, 1310-73-2), 96 uM of EDTA (Sigma, 60-00-4), and 20 g/L of glucose (Sigma, 50-99-7). A reaction was caused for over one day to finally decompose the peracetic acid and its reactants into acetic acid, water, and oxygen. Then, a peroxide test sticks (Quantofix Peroxide 100, Macherey-Nagel GmbH & Co., Germany) were used to determine whether the peracetic acid was decomposed.

In this regard, 1 L of the *Aurantiochytrium* medium was composed of 2 g of a yeast extract (Sigma, 8013-01-2), 2 g of peptone (Sigma, 91079-40-2), 20 g of D-glucose (Sigma, 50-99-7), 500 mL of seawater (Namhae Sea), and 500 mL of distilled water (Refer to Table 5)

TABLE 5

| Ingredients | Amount |
| --- | --- |
| Yeast extract | 2 g |
| Peptone | 2 g |
| D-glucose | 20 g |
| Seawater | 500 mL |
| Distilled water | 500 mL |
| Total | 1 L |

Comparative Example 1

The procedures were performed in the same manner as described in Example 1, excepting that EDTA was not used.

Comparative Example 2

The procedures were performed in the same manner as described in Example 1, excepting that glucose was not used.

Examples 2 to 6: Varied Glucose Concentration

The procedures were performed in the same manner as described in Example 1, excepting that the glucose was used in a varied amount of 10 g/L (Example 2), 30 g/L (Example 3), 40 g/L (Example 4), 50 g/L (Example 5), or 60 g/L (Example 6).

Examples 7 to 12: Varied Sucrose Concentration

The procedures were performed in the same manner as described in Example 1, excepting that sucrose was used in place of the glucose in a varied amount of 10 g/L (Example 7), 20 g/L (Example 8), 30 g/L (Example 9), 40 g/L (Example 10), 50 g/L (Example 11), or 60 g/L (Example 12).

Comparative Examples 3 to 9

The procedures were performed in the same manner as described in Example 1, excepting that $CaCl_2$ was added in place of $FeCl_3$ while not using EDTA (Comparative Example 3); $CaCl_2$ was added in place of $FeCl_3$ while using EDTA (Comparative Example 4); $FeSO_4$ was added in place of $FeCl_3$ while not using EDTA (Comparative Example 5); $MgCl_2$ was added in place of $FeCl_3$ while not using EDTA (Comparative Example 6); $MgCl_2$ was added in place of $FeCl_3$ while using EDTA (Comparative Example 7); $ZnCl_2$ was added in place of $FeCl_3$ while not using EDTA (Comparative Example 8); or $ZnCl_2$ was added in place of $FeCl_3$ while using EDTA (Comparative Example 9).

Example 13

The procedures were performed in the same manner as described in Example 1, excepting that $FeSO_4$ was added in place of $FeCl_3$.

Experimental Example 1: Effects of EDTA

The procedures were performed in the same manner as described in Example 1 and Comparative Example 1 in order to confirm the effects of EDTA in the decomposition of peracetic acid.

As a result, when EDTA was not used (Comparative Example 1, FIG. 1), the solubility of a metal ion, iron (Fe) ion dropped sharply to cause a considerable decrease in the decomposition rate of the peracetic acid, compared to when EDTA was used (Example 1, FIG. 2) (Refer to Table 1).

Figure 2:
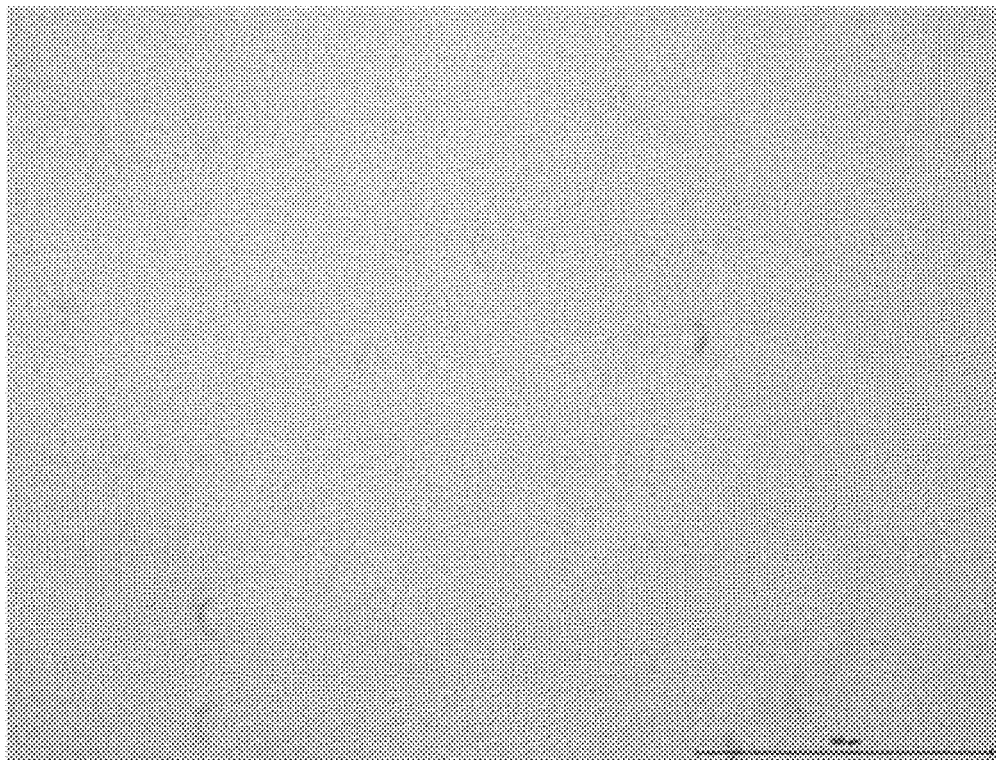
FIG. 2 is a microscopic image showing the agglomeration of iron ions during decomposition of peracetic acid without EDTA.

Further, when EDTA was not used (Comparative Example 1), the iron (Fe) ions condensed in other polymer molecules and combined with those polymer molecules as shown in FIG. 1, compared to when EDTA was used (Example 1, FIG. 2). This result suggests that the iron ions are soluble to water in the presence of EDTA to increase the decomposition rate of the peracetic acid, whereas, without EDTA, they are insoluble to water or combine with the other components to lower the decomposition rate of the peracetic acid.

TABLE 1

| Time (hour) | Example 1 PAA + N + G(20)FeCl$_3$ + EDTA | Comparative Example 1 PAA + N + G(20)FeCl$_3$ |
| --- | --- | --- |
| 0 | >200 | >200 |
| 6 | 100 | >200 |
| 12 | 0 | >200 |
| 18 | 0 | >200 |
| 24 | 0 | >200 |
| 30 | 0 | >200 |

Note)
N: NaOH,
G: Glucose,
F: FeCl$_3$,
F(E): FeCl$_3$ + EDTA
The numerals in the table indicate the concentration of the peracetic acid. For example, ">200" means that 200 mg/L or more of peracetic acid remains.

Experimental Example 2: Effects of Glucose

The procedures were performed in the same manner as described in Examples 1 to 6 and Comparative Example 2 in order to confirm the effects of glucose in the decomposition of peracetic acid.

As a result, the peracetic acid was almost not decomposed when glucose was not used, and the decomposition rate of the peracetic acid gradually increased with an increase in the amount of the glucose (Refer to Table 2).

TABLE 2

| Time (hour) | Comparative Example 2 PAAF(E) + N | Example 2 PAAF(E) + N + G(10) | Example 1 PAAF(E) + N + G(20) | Example 3 PAAF(E) + N + G(30) | Example 4 PAAF(E) + N + G(40) | Example 5 PAAF(E) + N + G(50) | Example 6 PAAF(E) + N + G(60) |
|---|---|---|---|---|---|---|---|
| 0 | >200 | >200 | >200 | >200 | >200 | >200 | >200 |
| 6 | >200 | >200 | 100 | 60 | 20 | 14 | 10 |
| 12 | >200 | 0 | 0 | 0 | 0 | 0 | 0 |
| 24 | >200 | 0 | 0 | 0 | 0 | 0 | 0 |

Note)
N: NaOH,
G: Glucose,
F: $FeCl_3$,
F(E): $FeCl_3$ + EDTA
The numerals in the table indicate the concentration of the peracetic acid. For example, ">200" means that 200 mg/L or more of peracetic acid remains.

Experimental Example 3: Effects of Sucrose

The procedures were performed in the same manner as described in Examples 7 to 12 and Comparative Example 2 in order to confirm the effects of sucrose in the decomposition of peracetic acid.

As a result, the peracetic acid was almost not decomposed when sucrose was not used, and the decomposition rate of the peracetic acid gradually increased with an increase in the amount of the sucrose (Refer to Table 3).

TABLE 3

| Time (hour) | Comparative Example 2 PAAF(E) + N | Example 7 PAAF(E) + N + S(10) | Example 8 PAAF(E) + N + S(20) | Example 9 PAAF(E) + N + S(30) | Example 10 PAAF(E) + N + S(40) | Example 11 PAAF(E) + N + S(50) | Example 12 PAAF(E) + N + S(60) |
|---|---|---|---|---|---|---|---|
| 0 | >200 | >200 | >200 | >200 | >200 | >200 | >200 |
| 6 | >200 | >200 | >200 | >200 | >200 | 160 | 140 |
| 12 | >200 | 0 | 0 | 0 | 0 | 0 | 0 |
| 24 | >200 | 0 | 0 | 0 | 0 | 0 | 0 |

Note)
N: NaOH,
G: Glucose,
S: Sucrose,
F: $FeCl_3$,
F(E): $FeCl_3$ + EDTA
The numerals in the table indicate the concentration of the peracetic acid. For example, ">200" means that 200 mg/L or more of peracetic acid remains.

Experimental Example 4: Effects of Metals

The procedures were performed in the same manner as described in Examples 1 and 13 and Comparative Examples 1 and 3 to 9 in order to confirm the effects of metals in the decomposition of peracetic acid.

As a result, the peracetic acid was decomposed very well in the presence of $FeCl_3$+EDTA or $FeSO_4$+EDTA; the peracetic acid was not decomposed in the presence of $CaCl_2$+EDTA, $MgCl_2$+EDTA, or $ZnCl_2$+EDTA; and the peracetic acid was almost not decomposed in the presence of a metal in the form of $FeCl_3$, $FeSO_4$, $CaCl_2$, $MgCl_2$, or $ZnCl_2$ other than EDTA (Refer to FIG. 4).

TABLE 4

| | Time (hour) | 0 | 12 | 24 |
|---|---|---|---|---|
| Example 1 | PAA + N + G(20)$Fe_2Cl_3$ + EDTA | >200 | 0 | 0 |
| Comparative Example 1 | PAA + N + G(20)$Fe_2Cl_3$ | >200 | >200 | >200 |
| Comparative Example 3 | PAA + N + G(20)$CaCl_2$ | >200 | >200 | >200 |
| Comparative Example 4 | PAA + N + G(20)$CaCl_2$ + EDTA | >200 | >200 | >200 |
| Comparative Example 5 | PAA + N + G(20)$FeSO_4$ | >200 | >200 | >200 |
| Example 13 | PAA + N + G(20)$FeSO_4$ + EDTA | >200 | 100 | 0 |
| Comparative Example 6 | PAA + N + G(20)$MgCl_2$ | >200 | >200 | >200 |
| Comparative Example 8 | PAA + N + G(20)$ZnCl_2$ | >200 | >200 | >200 |
| Comparative Example 9 | PAA + N + G(20)$ZnCl_2$ + EDTA | >200 | >200 | >200 |

Note)
N: NaOH,
G: Glucose,
S: Sucrose
The numerals in the table indicate the concentration of the peracetic acid. For example, ">200" means that 200 mg/L or more of peracetic acid remains.

MODE FOR THE IMPLEMENTATION OF THE INVENTION

Hereinafter, the present invention will be described in further detail.

The present invention provides a method for decomposing peracetic acid that includes the steps of: mixing peracetic acid with water; and adding an iron ion, an alkali metal hydroxide, ethylenediaminetetraacetic acid (EDTA), and a sugar to cause a reaction and decompose the peracetic acid into acetic acid, water and oxygen.

The term "sterilization" as used in the present invention means killing all the nutrient cells or spores of living microorganisms.

In the method for decomposing peracetic acid according to the present invention, the iron ion may be $Fe^{2+}$ or $Fe^{3+}$ and derived from a Fe-containing salt, such as $FeCl_3$, $FeCl_2$, or $FeSO_4$.

In the method for decomposing peracetic acid according to the present invention, the alkali metal hydroxide may include, but not limited to, LiOH, NaOH, or KOH.

In the method for decomposing peracetic acid according to the present invention, the alkali metal hydroxide, such as NaOH, may be used to easily acquire a pH value suitable for decomposition of peracetic acid (PAA), thereby causing the peracetic acid decomposed quickly.

In the method for decomposing peracetic acid according to the present invention, the ethylenediaminetetraacetic acid (EDTA) may increase the solubility of the iron ion to prevent the iron ion from combining with other substances, and thereby accelerate the decomposition of the peracetic acid.

In the method for decomposing peracetic acid according to the present invention, when the molar concentration of the added iron ion is similar to that of the EDTA, the decomposition rate of the peracetic acid may be higher than when the molar concentration of the iron ion is higher or lower than that of the EDTA. The decomposition rate of the peracetic acid may be highest when the molar concentration of the iron ion is the same as that of the EDTA. For example, the molar concentration ratio of iron ion to EDTA may be 10:1, 9:1, 8:1, 7:1, 6:1, 5:1, 4:1, 3:1, 2:1, or 1:1; or 1:2, 1:3, 1:4, 1:5, 1:6, 1:7, 1:8, 1:9, or 1:10. The quantity of EDTA being greater than that of the iron ion existing during the reaction may inhibit the Fenton reaction caused by the iron ion and hence the mechanism for decomposition of the peracetic acid driven by the iron.

In the method for decomposing peracetic acid according to the present invention, the sugar may be a carbon source for microorganisms and include, but not limited to, glucose, sucrose, or waste sugar (molasses).

Further, the concentration of the sugar may be 100 g/L or less, preferably 5 to 50 g/L.

In the method for decomposing peracetic acid according to the present invention, a basic buffer solution may be used as a substitute for the alkali metal hydroxide or may be further added. The basic buffer solution as used herein may be 4-(2-hydroxyethyl)-1-piperazineethanesulfonic acid (HEPES).

In the method for decomposing peracetic acid according to the present invention, the peracetic acid reacts with water to form acetic acid and hydrogen peroxide according to the following chemical equation.

$$CH_3CO_3H + H_2O \rightarrow H_2O_2 + CH_3CO_2H \qquad \text{i)}$$

The hydrogen peroxide produced from the reaction of the peracetic acid and water is susceptible to the Fenton reaction driven by the iron ion and decomposed into acetic acid, water and oxygen according to the following chemical equations.

$$2CH_3CO_3H \rightarrow 2CH_3CO_2H + O_2 \qquad \text{ii)}$$

$$2H_2O_2 \rightarrow 2H_2O + O_2 \qquad \text{iii)}$$

The present invention also provides a method for sterilizing a medium that includes the steps of: adding peracetic acid to a medium containing a sugar and a nitrogen source to cause a reaction for sterilization; and adding an iron ion, an alkali metal hydroxide, and ethylenediaminetetraacetic acid (EDTA) as accelerators for decomposition of peracetic acid to the sterilized medium and causing a reaction between the peracetic acid and the accelerator for decomposition of peracetic acid in the medium to decompose the peracetic acid into acetic acid, water and oxygen.

In the method for sterilizing a medium according to the present invention, the peracetic acid and the peracetic acid reactant contained in the sterilized medium can be finally decomposed into acetic acid, water and oxygen and thus removed from the sterilized medium. The medium removed of acetic acid, water and oxygen may be available for the cultivation of microorganisms.

In the method for sterilizing a medium according to the present invention, the medium may be a medium that requires sugar (glucose, sucrose, waster sugar, etc.) as in the case of culturing yeasts, *Aurantiochytrium*, or the like.

In the method for sterilizing a medium according to the present invention, the medium may be a medium that requires light as in the case of culturing microalgae, occurring in seawater or freshwater.

In the method for sterilizing a medium according to the present invention, the iron ion may be $Fe^{2+}$ or $Fe^{3+}$ and derived from a Fe-containing salt, such as $FeCl_3$, $FeCl_2$, or $FeSO_4$.

In the method for sterilizing a medium according to the present invention, the alkali metal hydroxide may include, but not limited to, LiOH, NaOH, or KOH.

In the method for sterilizing a medium according to the present invention, the alkali metal hydroxide, such as NaOH, may be used to easily acquire a pH value suitable for decomposition of peracetic acid (PAA), thereby causing the peracetic acid decomposed quickly.

In the method for sterilizing a medium according to the present invention, the ethylenediaminetetraacetic acid (EDTA) may increase the solubility of the iron ion to prevent the iron ion from combining with other substances, and thereby accelerate the decomposition of the peracetic acid.

In the method for sterilizing a medium according to the present invention, when the molar concentration of the added iron ion is similar to that of the EDTA, the decomposition rate of the peracetic acid may be higher than when the molar concentration of the iron ion is higher or lower than that of the EDTA. The decomposition rate of the peracetic acid may be highest when the molar concentration of the iron ion is the same as that of the EDTA.

In the method for sterilizing a medium according to the present invention, the sugar may include, but not limited to, glucose, sucrose, or waste sugar (molasses).

Further, the concentration of the sugar may be 100 g/L or less, preferably 5 to 50 g/L. In the method for sterilizing a medium according to the present invention, a basic buffer solution may be used as a substitute for the alkali metal hydroxide or may be further added. The basic buffer solution as used herein may be 4-(2-hydroxyethyl)-1-piperazineethanesulfonic acid (HEPES).

The sterilization of a medium performed by the method of the present invention has an advantage of storing a medium for a long time without autoclaving until neutralization or being contaminated even in an open container.

The present invention also provides a method for culturing microorganisms that includes the steps of: adding a medium sterilized by the method of claim 6 to a bioreactor; and inoculating microorganisms into the added medium and conducting a pure cultivation.

In the method for culturing microorganisms according to the present invention, the microorganisms may include, but not limited to, at least one selected from the group consisting of *Aurantiochytrium* sp., *Schizochytrium* sp., *Chlorella* sp., *Synechocystis* sp., *Debaryomyces* sp., Yeasts, Lactic acid bacteria, Actinomycetes, *Euglena, Mortierella* filamentous fungus, and photosynthetic bacteria.

The present invention also provides a method for sterilizing a bioreactor and a medium at the same time by placing a medium containing a sugar and a nitrogen source in a bioreactor and then adding peracetic acid to cause a sterilization reaction.

In accordance with an embodiment of the present invention, it was confirmed that when peracetic acid was added to an *Aurantiochytrium* medium to cause a reaction for 2 hours for sterilization of the medium and then $FeCl_3$, NaOH, EDTA, and glucose were added to the sterilized medium to cause a reaction for one day or longer, the peracetic acid was decomposed into acetic acid, water and oxygen at a considerably high decomposition rate (Refer to Experimental Example 1).

In accordance with an embodiment of the present invention, it was confirmed that when peracetic acid was added to an *Aurantiochytrium* medium to cause a reaction for 2 hours for sterilization of the medium and then $FeCl_3$, NaOH, and glucose other than EDTA were added to the sterilized medium to cause a reaction for one day or longer, the decomposition rate of the peracetic acid was remarkably reduced (Refer to Experimental Example 1).

In accordance with an embodiment of the present invention, it was confirmed that when peracetic acid was added to an *Aurantiochytrium* medium to cause a reaction for 2 hours for sterilization of the medium and then $FeCl_3$, NaOH, and EDTA were added to the sterilized medium with glucose added in an increasing amount to cause a reaction for one day or longer, the decomposition rate of the peracetic acid into acetic acid, water and oxygen was gradually increased with an increase in the added amount of the glucose (Refer to Experimental Example 2).

In accordance with an embodiment of the present invention, it was confirmed that when peracetic acid was added to an *Aurantiochytrium* medium to cause a reaction for 2 hours for sterilization of the medium and then $FeCl_3$, NaOH, and EDTA other than glucose were added to the sterilized medium to cause a reaction for one day or longer, the decomposition rate of the peracetic acid was significantly reduced (Refer to Experimental Example 2). As a result, such a reducing sugar as glucose reduced the iron oxidized by the peracetic acid to activate the Fenton reaction driven by iron, thereby aiding the iron-driven decomposition of the peracetic acid.

In accordance with an embodiment of the present invention, it was confirmed that when peracetic acid was added to an *Aurantiochytrium* medium to cause a reaction for 2 hours for sterilization of the medium and then $FeCl_3$, NaOH, and EDTA were added to the sterilized medium with sucrose added in an increasing amount to cause a reaction for one day or longer, the decomposition rate of the peracetic acid into acetic acid, water and oxygen was gradually increased with an increase in the added amount of the sucrose (Refer to Experimental Example 3).

In accordance with an embodiment of the present invention, it was confirmed that when peracetic acid was added to an *Aurantiochytrium* medium to cause a reaction for 2 hours for sterilization of the medium and then a metal, NaOH, glucose, and EDTA were added to the sterilized medium to cause a reaction for one day or longer, the peracetic acid was decomposed very well in the presence of $FeCl_3$+EDTA or $FeSO_4$+EDTA; the peracetic acid was almost not decomposed in the presence of $CaCl_2$+EDTA, $MgCl_2$+EDTA, or $ZnCl_2$+EDTA; and the peracetic acid was almost not decomposed in the presence of a metal in the form of $FeCl_3$, $FeSO_4$, $CaCl_2$, $MgCl_2$, or $ZnCl_2$ other than EDTA (Refer to Experimental Example 4).

INDUSTRIAL APPLICABILITY

The cultivation of microorganisms using the decomposition method for peracetic acid and the culturing method for microorganisms using the decomposition method according to the present invention allows a complete sterilization of a bioreactor and a culture medium without heat and thus acquires industrial availability.

What is claimed is:
1. A method for decomposing peracetic acid, comprising:
   (1) mixing peracetic acid with water; and
   (2) adding an iron ion, an alkali metal hydroxide, ethylenediaminetetraacetic acid (EDTA), and a sugar to cause a reaction and decompose the peracetic acid into acetic acid, water and oxygen.
2. The method according to claim 1, wherein the iron ion is $Fe^{2+}$ or $Fe^{3+}$.
3. The method according to claim 2, wherein the iron ion is $Fe^{2+}$.
4. The method according to claim 2, wherein the iron ion is $Fe^{3+}$.
5. The method according to claim 1, wherein the sugar is glucose, sucrose, or waste sugar.
6. The method according to claim 5, wherein the concentration of the sugar is 100 g/L or less.
7. The method according to claim 6, wherein the concentration of the sugar is 5 to 50 g/L.
8. The method according to claim 1, wherein a basic buffer solution is further added.
9. The method according to claim 1, wherein the molar concentration of the iron ion is the same as the molar concentration of the EDTA.
10. A method for sterilizing a medium, comprising:
    (1) adding peracetic acid to a medium containing a sugar and a nitrogen source to cause a reaction for sterilization; and
    (2) adding an iron ion, an alkali metal hydroxide, and ethylenediaminetetraacetic acid (EDTA) as accelerators for decomposition of peracetic acid to the sterilized medium and causing a reaction between the peracetic acid and the accelerators for decomposition of peracetic acid in the medium to decompose the peracetic acid into acetic acid, water and oxygen.
11. The method according to claim 10, wherein the iron ion is $Fe^{2+}$ or $Fe^{3+}$.
12. The method according to claim 10, wherein the sugar is glucose, sucrose, or waste sugar.

13. The method according to claim 10, wherein the concentration of the sugar is 100 g/L or less.

14. The method according to claim 10, wherein a basic buffer solution is further added.

\* \* \* \* \*